United States Patent
Wilkins

(10) Patent No.: US 11,801,151 B2
(45) Date of Patent: Oct. 31, 2023

(54) ANATOMIC SHELL 2-IN-1 WINDOW TRIAL

(71) Applicant: Howmedica Osteonics Corp., Mahwah, NJ (US)

(72) Inventor: Sean Brian Wilkins, Hoboken, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 652 days.

(21) Appl. No.: 16/813,845

(22) Filed: Mar. 10, 2020

(65) Prior Publication Data

US 2020/0289292 A1    Sep. 17, 2020

Related U.S. Application Data

(60) Provisional application No. 62/817,209, filed on Mar. 12, 2019.

(51) Int. Cl.
*A61F 2/46* (2006.01)
*A61F 2/34* (2006.01)
*A61F 2/30* (2006.01)

(52) U.S. Cl.
CPC ........ *A61F 2/4684* (2013.01); *A61F 2/30749* (2013.01); *A61F 2/34* (2013.01); *A61F 2/4609* (2013.01); *A61F 2002/3483* (2013.01)

(58) Field of Classification Search
CPC ........ A61F 2002/4687; A61F 2002/343; A61F 2002/3432; A61F 2002/3479
See application file for complete search history.

(56) References Cited

U.S. PATENT DOCUMENTS

| 4,528,980 | A |   | 7/1985 | Kenna |   |
|---|---|---|---|---|---|
| 5,702,478 | A |   | 12/1997 | Tornier |   |
| 5,925,077 | A | * | 7/1999 | Williamson | A61F 2/4609 623/22.34 |

(Continued)

FOREIGN PATENT DOCUMENTS

| WO | 2013126416 A1 | 8/2013 |   |
|---|---|---|---|
| WO | 2014063226 A1 | 5/2014 |   |
| WO | WO-2015165817 A1 * | 11/2015 | A61B 17/1746 |

OTHER PUBLICATIONS

Restoration Anatomic Acetabular System, Surgical Technique, Stryker Orthopaedics, Copyright 2015.

*Primary Examiner* — Brian A Dukert
*Assistant Examiner* — Melissa A Hoban
(74) *Attorney, Agent, or Firm* — Lerner David LLP

(57) ABSTRACT

A trial template for visualizing the placement of a bone screw includes a bone facing side, a visualization side opposite the bone facing side, a trial periphery defining an outer perimeter of the trial, and first and second support members positioned within the trial periphery and each having a length extending in a direction transverse to an axis that extends through the bone facing and visualization sides The first and second support members define a viewing window therebetween that extends through the second component from the visualization side to the bone facing side. The trial template also includes a visualization member extending between the first and second support members and across the viewing window. The visualization member includes a position within the second component periphery that corresponds with a desired bone screw location in a bone.

10 Claims, 3 Drawing Sheets

(56) References Cited

U.S. PATENT DOCUMENTS

| | | |
|---|---|---|
| 7,896,883 B2 | 3/2011 | Ek et al. |
| 8,192,453 B2 | 6/2012 | Valla |
| 8,231,682 B2 | 7/2012 | Lafosse et al. |
| 8,366,713 B2 | 2/2013 | Long et al. |
| 8,551,177 B2 | 10/2013 | De Wilde et al. |
| 8,568,487 B2* | 10/2013 | Witt .................... A61F 2/30771 |
| | | 623/22.24 |
| 8,579,985 B2 | 11/2013 | Podolsky et al. |
| 8,608,749 B2 | 12/2013 | Meridew et al. |
| 9,033,990 B2 | 5/2015 | Iannotti et al. |
| 9,060,788 B2 | 6/2015 | Bollinger |
| 9,119,643 B2 | 9/2015 | Winslow et al. |
| 9,161,843 B2 | 10/2015 | Deffenbaugh et al. |
| 9,204,977 B2 | 12/2015 | Bollinger |
| 9,211,128 B2 | 12/2015 | Gillman et al. |
| 9,301,858 B2 | 4/2016 | Barsoum et al. |
| 9,339,278 B2 | 5/2016 | Meridew et al. |
| 9,351,743 B2 | 5/2016 | Kehres et al. |
| 9,386,993 B2 | 7/2016 | Meridew et al. |
| 9,498,233 B2* | 11/2016 | Eash .................... A61F 2/4609 |
| 9,517,145 B2* | 12/2016 | Meridew ............ A61B 17/1746 |
| 9,561,040 B2 | 2/2017 | Winslow |
| 9,610,084 B2 | 4/2017 | Walker |
| 9,615,839 B2 | 4/2017 | Olson |
| 9,661,040 B2 | 5/2017 | Kobayashi |
| 9,741,263 B2 | 8/2017 | Iannotti et al. |
| 9,775,716 B2 | 10/2017 | Goldberg |
| 9,814,471 B2 | 11/2017 | Goldberg et al. |
| 9,820,868 B2 | 11/2017 | Witt et al. |
| 9,839,436 B2 | 12/2017 | Kehres et al. |
| 9,943,319 B2 | 4/2018 | Fortin et al. |
| 10,034,757 B2 | 7/2018 | Kovacs et al. |
| 10,034,777 B2 | 7/2018 | Kovacs et al. |
| 2004/0193278 A1 | 9/2004 | Maroney et al. |
| 2008/0009952 A1* | 1/2008 | Hodge ...................... A61F 2/34 |
| | | 623/22.21 |
| 2009/0132045 A1 | 5/2009 | Lafosse |
| 2009/0204225 A1* | 8/2009 | Meridew ............. A61F 2/30734 |
| | | 606/301 |
| 2009/0270993 A1 | 10/2009 | Maisonneuve et al. |
| 2011/0208202 A1 | 8/2011 | Zumsteg et al. |
| 2012/0109137 A1* | 5/2012 | Iannotti .............. A61B 17/1728 |
| | | 606/87 |
| 2012/0310360 A1 | 12/2012 | Parrott et al. |
| 2014/0142578 A1 | 5/2014 | Hananouchi et al. |
| 2014/0163565 A1* | 6/2014 | Bollinger ........... A61B 17/1746 |
| | | 606/91 |
| 2014/0276870 A1* | 9/2014 | Eash .................. A61B 17/8897 |
| | | 606/91 |
| 2015/0066149 A1 | 3/2015 | Parrott et al. |
| 2015/0265288 A1 | 9/2015 | Guederian |
| 2015/0289992 A1 | 10/2015 | Anglin et al. |
| 2016/0249939 A1 | 9/2016 | Richter et al. |
| 2016/0287408 A1* | 10/2016 | Witt .................... A61B 17/8872 |
| 2016/0310285 A1 | 10/2016 | Kovacs et al. |
| 2016/0374696 A1 | 12/2016 | Kehres et al. |
| 2016/0374697 A1 | 12/2016 | Kehres et al. |
| 2017/0238942 A1 | 8/2017 | Fortin et al. |
| 2017/0304063 A1 | 10/2017 | Hatzidakis et al. |
| 2018/0028202 A1 | 2/2018 | Nelson et al. |
| 2018/0103967 A1 | 4/2018 | Rouyer et al. |

* cited by examiner

ANATOMIC SHELL 2-IN-1 WINDOW TRIAL

CROSS-REFERENCE TO RELATED APPLICATIONS

This application claims the benefit of the filing date of U.S. Provisional Patent Application No. 62/817,209, filed Mar. 12, 2019, the disclosure of which is hereby incorporated herein by reference.

BACKGROUND OF THE INVENTION

Joint arthroplasty procedures involve the replacement of a natural joint surface with an artificial joint surface. This generally involves removing a certain amount of native bone and attaching the artificial prosthesis to the resected bone. As joint arthroplasty procedures are often performed on diseased or damaged joints, it is common that the underlying bone to which the joint prosthesis is attached is also diseased or damaged in a way that can affect the structural support needed for proper functioning of the artificial joint prosthesis and for long-term fixation thereof.

For example, fixation means, such as bone screws, may be deployed to secure prosthetic components to bone. However, the underlying bone may be weakened in certain areas due to damage or disease, such as osteolysis and the like, such that the bone is not adequate to support the fixation means. Visual inspection can help distinguish regions of healthy bone from those of unhealthy bone so that the operator can utilize the healthy bone to secure the prosthesis thereto. However, currently existing surgical instruments often obscure the underlying bone making it difficult to determine whether or not the means for fixing the prosthesis to the bone has adequate support prior to the deployment of the same. Moreover, such surgical instruments are often configured for one bone or another (i.e., right or left) resulting in a cluttering of the operating theater and a high demand on sterilization resources. Thus, further improvements are desirable.

BRIEF SUMMARY OF THE INVENTION

In one aspect of the present disclosure, an arthroplasty system includes a first component that includes a convex side configured to engage one of an acetabulum and glenoid cavity, a concave side opposite the convex side, a first component periphery that defines an outer perimeter of the first component and is defined by a convergence of the convex and concave sides, and a tool opening that extends through the first component from the concave side to the convex side and is configured to receive at least one of a bone screw or drill bit. The tool opening includes a center point defined by an axis extending along a length of the tool opening. The system also includes a second component separate from the first component. The second component includes a bone facing side, a visualization side opposite the bone facing side, and a second component periphery that defines an outer perimeter of the second component and that substantially corresponds to the first component periphery. The second component also has first and second support members and a first visualization member. The first and second support members each include a length extending in a direction transverse to an axis that extends through the bone facing and visualization sides within the second component periphery. The first and second support members define a viewing window therebetween that extends through the second component from the visualization side to the bone facing side. The first visualization member extends between the first and second support members and across the viewing window. The first visualization member includes a position relative to the second component periphery that corresponds with a position of the center point of the tool opening relative to the first component periphery.

Additionally, the first component may be a drill guide. Alternatively, the first component may be a prosthesis that includes an articular surface at the concave side. The concave side may further include a rim extending at least partially about the concave articular surface. The opening of the first component may extend through the rim and the convex surface. The first support member may partially include the second component periphery. The first and second support members may be arcuate. Also, the first visualization member may be elongate and may extend along a straight longitudinal axis that extends from the first support member to the second support member. The position of the center point of the tool opening may be intersected by the longitudinal axis of the first visualization member when the first component is overlaid with the second component.

Continuing with this aspect, the system may further include a second visualization member adjacent the first visualization member. Also, the system may further include a third component that has a tool opening extending therethrough from a convex side to a concave side thereof. The second visualization member may correspond to the tool opening of the third component where the first component may be configured for engagement with a right acetabulum or glenoid cavity and the third component may be configured for engagement with a left acetabulum or glenoid cavity.

In another aspect of the present disclosure, a trial template for visualizing the placement of a bone screw includes a bone facing side, a visualization side opposite the bone facing side, a trial periphery defining an outer perimeter of the trial, and first and second support members positioned within the trial periphery. The first and second support members each have a length that extends in a direction transverse to an axis that extends through the bone facing and visualization sides. The first and second support members define a viewing window therebetween that extends through the second component from the visualization side to the bone facing side. The trial template also includes a visualization member that extends between the first and second support members and across the viewing window. The visualization member has a position within the second component periphery that corresponds with a desired bone screw location in a bone.

Additionally, the trial template may include a template portion that defines the trial periphery. Also, the trial periphery may be rounded. The first support member may include a portion of the trial periphery, and the second support member may be offset radially inwardly from the first support member. The visualization member may be one of a plurality of visualization members that each extend from the first support member to the second support member and across the viewing window. The visualization members may be spaced at predetermined intervals such that each visualization member corresponds to a desired bone screw location in the bone.

In a further aspect of the present disclosure, a method of implanting a prosthesis into a bone cavity includes placing a template over the bone cavity such that a visualization member thereof is positioned over a first location. The visualization member may extend between first and second support members and across a viewing window defined by first and second support members. The method also includes assessing a quality of bone at the first location by looking through the viewing window adjacent the visualization member, removing the template from the bone cavity, inserting a prosthesis into the bone cavity, and inserting a bone screw into the bone at the first location and through a screw opening of the prosthesis.

Additionally, the bone cavity may be one of an acetabulum or glenoid. Also, the placing step may include inserting a convex portion of the template into the cavity such that the convex portion abuts the bone within the bone cavity. Further, the placing step may include sliding the template over an elongate shaft extending from the bone. The removing step may also include sliding the template off of the elongate shaft. The method may also include reaming the bone cavity prior to the placing step, and also marking the bone relative to a reference mark on the template. Inserting the prosthesis into the bone cavity may include aligning a reference mark on the prosthesis with the marking on the bone.

BRIEF DESCRIPTION OF THE DRAWINGS

The features, aspects, and advantages of the present invention will become better understood with regard to the following description, appended claims, and accompanying drawings in which:

DETAILED DESCRIPTION

Figure 1A:
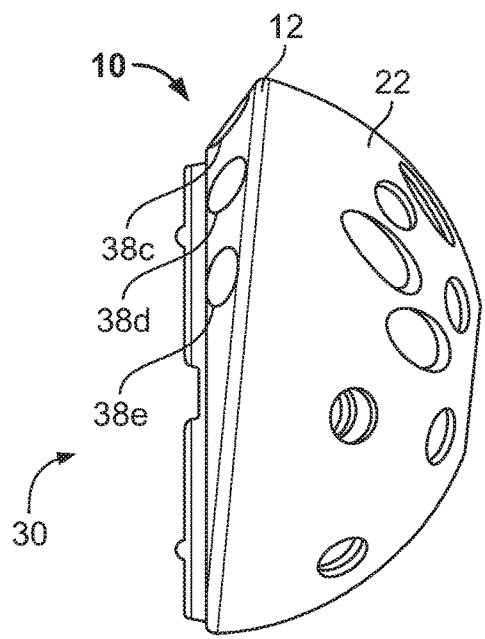
FIG. 1A is a side elevational view of a prosthesis according to an embodiment of the present disclosure.
Figure 1B:
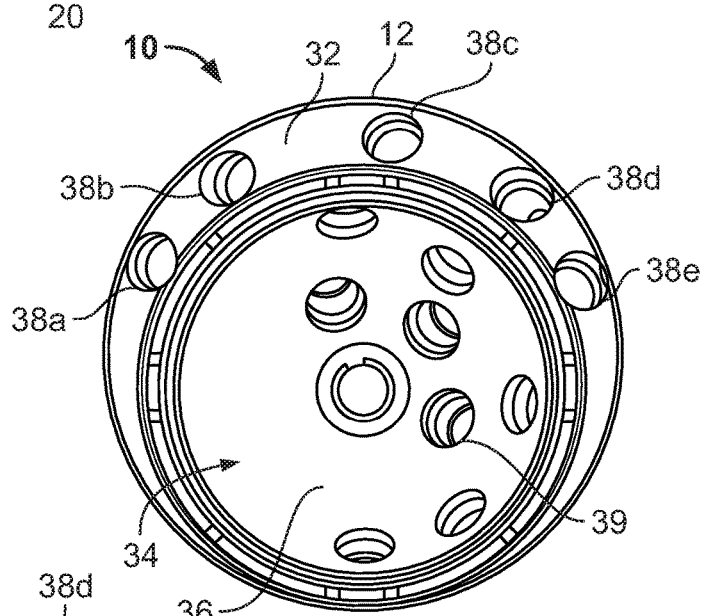
FIG. 1B is a front elevational view of the prosthesis of FIG. 1A.
Figure 1C:
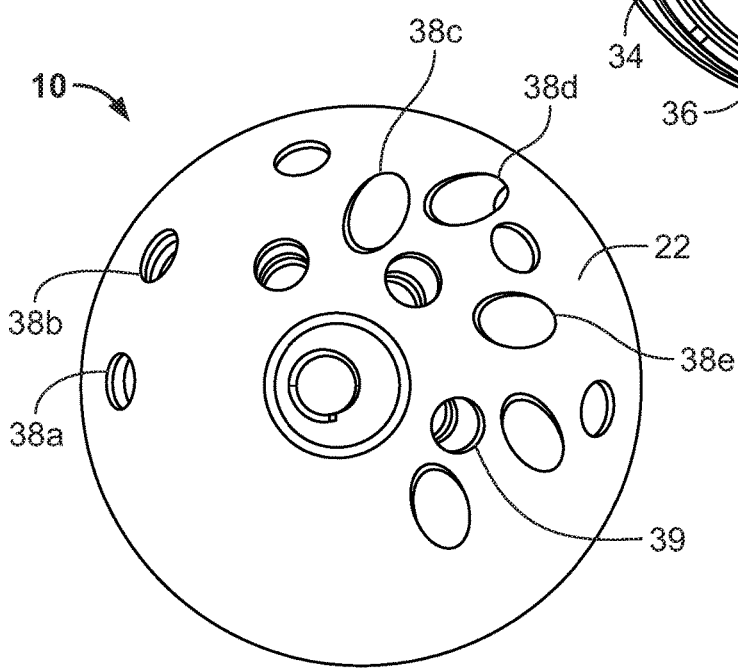
FIG. 1C is a rear elevational view of the prosthesis of FIG. 1A.

When referring to specific directions in the following discussion of certain implantable devices, it should be understood that such directions are described with regard to the implantable device's orientation and position during exemplary application to the human body. Thus, as used herein, the term "proximal" means close to the heart and the term "distal" means more distant from the heart. The term "inferior" means toward the feet and the term "superior" means toward the head. The term "anterior" means toward the front of the body or the face, and the term "posterior" means toward the back of the body. The term "medial" means toward the midline of the body, and the term "lateral" means away from the midline of the body. Also, as used herein, the terms "about," "generally" and "substantially" are intended to mean that slight deviations from absolute are included within the scope of the term so modified FIGS. 1A-1C depict a first component or shell prosthesis 10 according to an embodiment of the present disclosure. In the particular embodiment depicted, shell prosthesis 10 is an acetabular shell of an acetabular cup prosthesis which would also include a polymer insert (not shown). However, it should be understood that other forms of shell prostheses, such as those configured for a glenoid cavity, may be utilized without departing from the present invention. Prosthesis 10 generally includes a convex side or bone contact side 20 and a concave side or articular side 30. Convex side 20 includes a convex surface or bone contact surface 22. Bone contact surface 22 may include a structure to promote bone ingrowth when cup prosthesis is press-fit into a cavity of a bone.

Concave side 30 of prosthesis includes a shell opening 34 which is configured to receive the polymer insert for articulation with a corresponding prosthesis, such as a femoral or humeral prosthesis. Shell opening 34 is defined by a concave inner surface 36. In the particular embodiment depicted a rim 32 extends about shell opening 34 of concave side 30. The convergence of concave side 30 and convex side 20 defines a periphery of prosthesis which in turn forms a perimeter 12 of both concave side 30 and convex side 20. Such perimeter 12 is at least partially defined by rim. Rim 32 has a tapering width in its extension both clockwise and counterclockwise about shell opening 34. Such width is defined between perimeter 12 and shell opening 34.

Prosthesis 10 also includes a plurality of tool openings 38a-e that extend entirely through prosthesis 10 from rim 32 to bone contact surface 22. In addition, tool openings 39 extend entirely through prosthesis 10 from concave inner surface 36 to bone contact surface 22. Such tool openings 38, 39 are configured to receive a drill bit so as form a pilot hole in the bone, and a bone screw so as to securely fix prosthesis 10 to underlying bone.

FIGS. 2A-2D depict a second component or window/trial template 100 according to an embodiment of the present disclosure. Trial template 100 generally includes a convex side or bone facing side 110 and concave or visualization side 120. Convex and concave sides 110, 120 converge at a template periphery that defines a perimeter 102 of convex and concave sides 110, 120. Such perimeter 102 corresponds to perimeter 12 of prosthesis 10 such that template 100 has virtually the same geometry and peripheral dimensions as that of prosthesis 10.

Trial template 100 also includes a first support member 122, second support member 126, and convex portion or distal portion 110. First and second support members 122, 126 are connected such that they form a proximal portion 119 of template 100, and distal portion 118 extends distally from first and second support members 122, 126. First and second support members 122, 126 are both circular such that they collectively define perimeter 102 which is correspondingly circular. First support member 122 has a cross-sectional dimension smaller than that of second support member 126. First support member 122 is positioned within second support member 126 in an offset relationship such that first and second support members 122, 126 are not concentric with each other. In this regard, first and second support members 122, 126 define a crescent-shaped viewing window or first viewing window 108a that extends between portions of first and second support members 122, 126. In the embodiment depicted, first viewing window 108a is located at a superior end or first end of template 100 while at an inferior end or second end of template 100 first and second support members 122, 126 converge into each other such that first viewing window 108a tapers to an end at their interface. First and second support members 122, 126 are both hollow such that a second viewing window 108b, which is defined by an inner surface of first support member 122, extends entirely through template 100 in a proximal-distal direction. Similarly, first viewing window 108a extends entirely through template 100.

First and/or second support members 122, 126 include alignment markings 104a-b that can be aligned with markings on the bone, particular anatomy, or general directions such as superior and inferior in order to help set the alignment/rotational orientation of trial template 100 relative to the bone. As shown, in FIG. 2A, a first alignment marking 104a is configured to help properly orient template in a first bone, such as a right acetabulum or glenoid, and a second alignment marking 104b is configured to help properly orient template 100 in a second bone, such as a left acetabulum or glenoid.

Figure 2A:
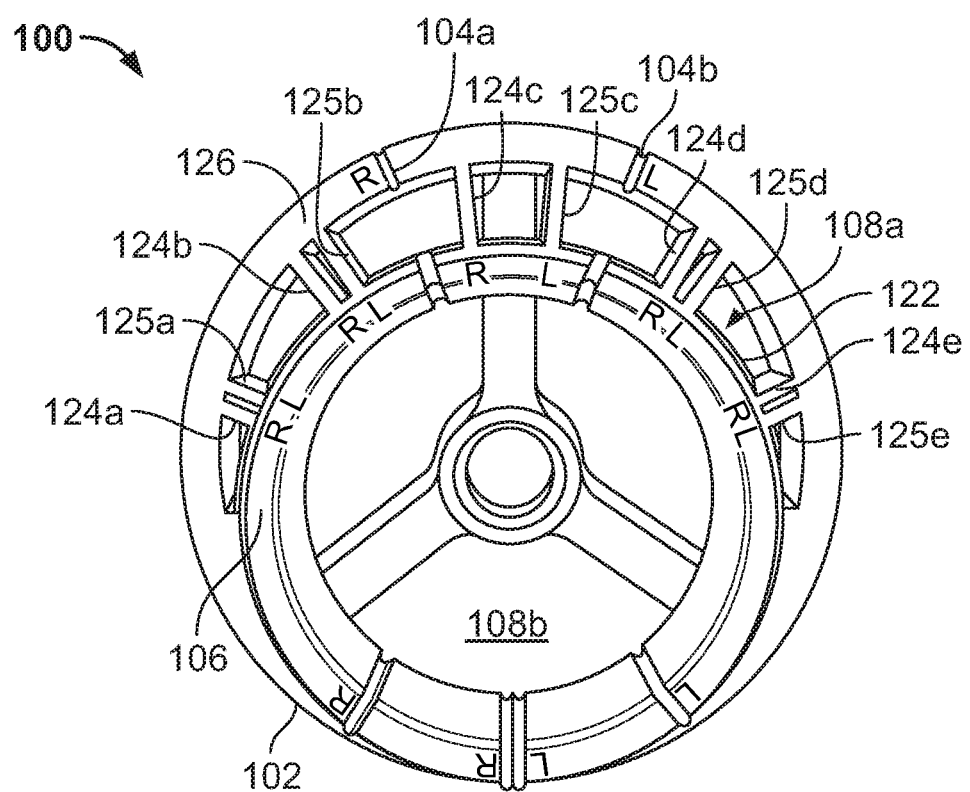
FIG. 2A is a front elevational view of a template according to an embodiment of the present disclosure.
Figure 2B:
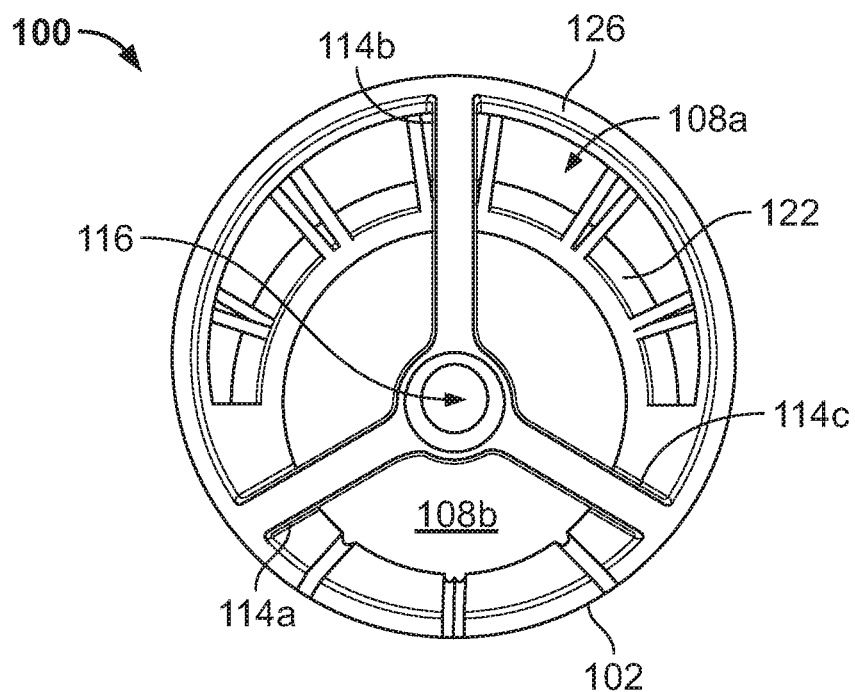
FIG. 2B is a rear elevational view of the template of FIG. 2A.
Figure 2C:
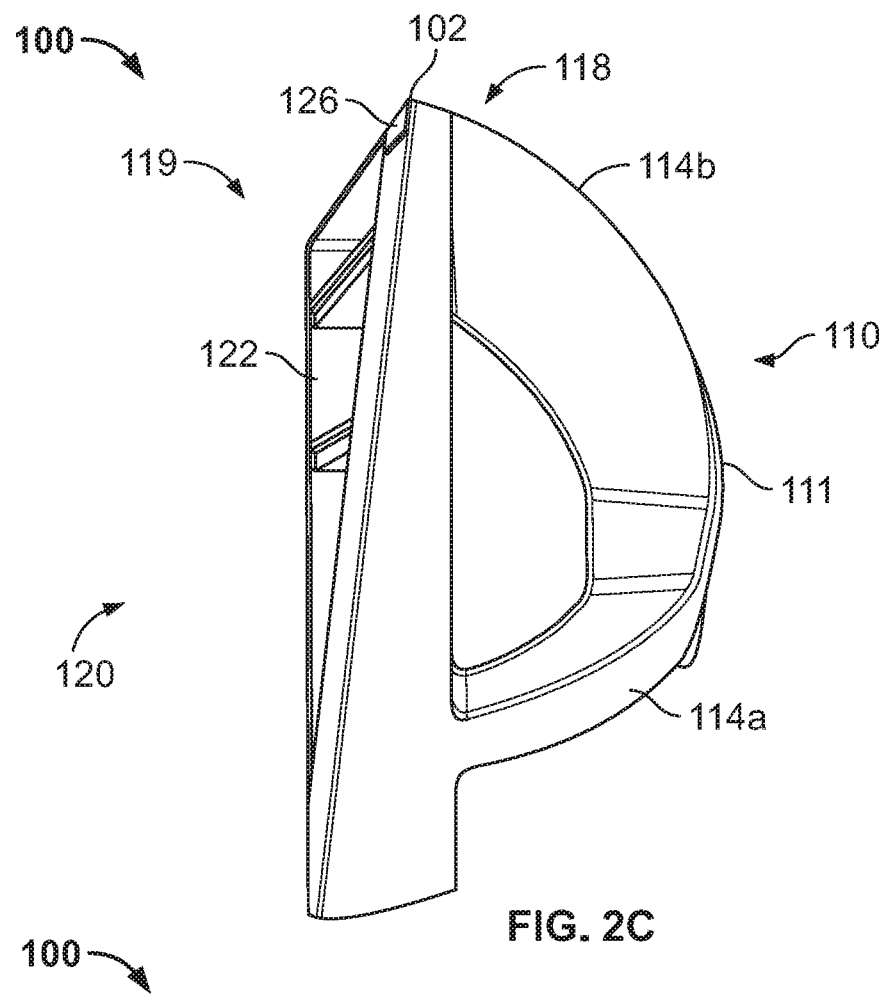
FIG. 2C is a side elevational view of the template of FIG. 2A.
Figure 2D:
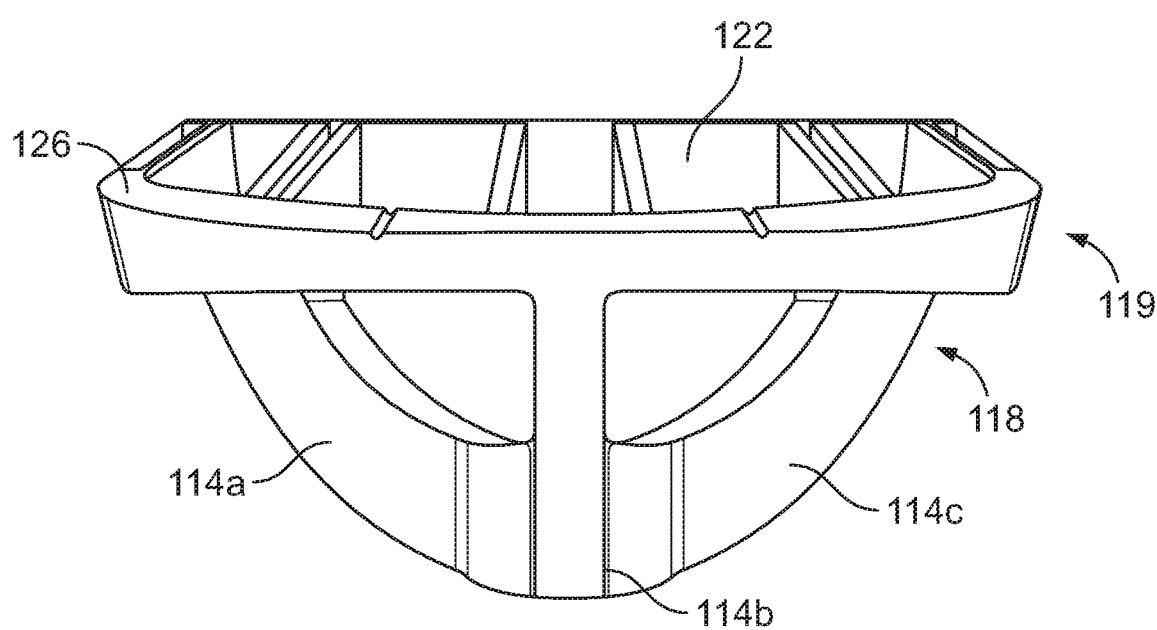
FIG. 2D is a top view of the template of FIG. 2A.

Trial template 100 also includes a plurality of visualization members 124, 125, as best shown in FIGS. 2A and 2B. Visualization members 124, 125 are depicted as elongate beams that extend between first and second support member 122, 126 and across first viewing window 108a. Visualization members 124, 125 are located within the periphery of trial template 100 such that they each correspond to a tool opening in a prosthesis, such as tool openings 38a-e. More particularly, trial template includes a first set of visualization members 124a-e that are located relative to first alignment marking 104a such that the first set of visualization members 124a-e are configured for use relative to a right variant of a bone, while a second set of visualization members 125a-e are located relative to second alignment marking 104b such that they are configured for use relative to a left variant of a bone. In other words, when first alignment marking 104a is aligned with a marking or particular anatomy of a right variant of bone, the first set of visualization members 124a-e are in a predetermined position for that bone. Second visualization members 125a-e and alignment marking 104b are similarly configured for a left variant of bone. In this regard, template 100 is universal to left and right variants of a bone and thus minimizes the total number of instruments present in an operating theater. Indicia 106 on trial member helps an operator determine which visualization members 124, 125 are for which bone.

Also, in the particular embodiment depicted, each of the first and second sets of visualization members 124a-e, 125a-e includes five visualization members which each correspond to a respective tool opening in a prosthesis. However, it should be understood that more or less visualization members 124, 125 may be utilized depending on the tool openings of the prosthesis that are desirable for visualization via trial template 100. In the depicted embodiment, it is desired to visualize tool openings 38a-e of prosthesis 10. Thus, second set of visualization members 125a-e are arranged to correspond to tool openings 38a-e of prosthesis as prosthesis 10 is configured for a left acetabulum as are visualization members 125a-e. However, first set of visualization members 124a-e correspond to tool openings of a second prosthesis or third component (not shown) that is configured for a right acetabulum and is basically a mirror image of prosthesis 10. Such correspondence means that, where template 100 is overlaid onto a corresponding prosthesis, such as prosthesis 10, visualization members 124a-e or 125a-e, depending on the prosthesis, would dissect its corresponding tool opening such that each visualization member 124a-e or 125a-e intersects the center point of the respective tool opening. The center point of each tool opening, such as openings 38a-e, is coincident with a central axis of such opening. So, while not every tool opening extends through its prosthesis in the same orientation (i.e., parallel with each other), such tool openings nonetheless have a center point at the proximal side or concave side of the prosthesis. For example, visualization members 125 a-e are configured to align with the center points of tool openings 38a-e at this proximal side 30 of prosthesis 10, rather than the distal or convex side 20 of prosthesis. Stated differently, tool openings 38a-e may extend through prosthesis 10 at different angles such that a center point of each tool opening 38a-e at proximal side 30 of prosthesis 10 is offset relative to that of distal side 20. Visualization members 125a-e are configured to align with the center point at proximal side 30 of prosthesis 10. Visualization members 124a-e are similarly configured to a second prosthesis. Thus, each visualization member 124, 125 is spaced at predetermined intervals relative to each other with the viewing window 108a surrounding each visualization member 124, 125. The low profile nature of visualization members 124, 125 provides visual clearance for an operator to inspect the underlying bone through window 108a directly underneath such visualization members 124, 125. This allows the operator to determine the health of the bone at the precise location through which a bone screw will be driven. In addition, it allows the operator to inspect the seating of the distal and proximal portions 118, 119 of template 100 relative to the bone to determine if further refinements of the resected bone surfaces are needed to appropriately receive prosthesis 10.

Distal portion 118 of template has a convex exterior such that it has a convex curvature similar to that of bone contact surface 22 of prosthesis 10. However, distal portion 118 has a concave interior. Distal portion 118 is comprised of a plurality of arm members 114 that extend from the proximal portion 119 of template 100 and curve inwardly to a distal apex 111 where arm members 114 intersect. In the embodiment depicted, there are three arm members 114a-c which define a cylindrical opening 116 at the distal apex 111. It should be understood that more or less arm members 114 may be utilized. However, three arm members 114a-c is preferable as it allows for three points of contact for stability while simultaneously maximizing the viewing space around such arm members 114a-c to visualize underlying bone. Cylindrical opening 116 is configured to receive a guide shaft (not shown) which may be pre-positioned within the bone so as to guide template 100 to a predetermined position relative to the bone. However, in some embodiments, cylindrical opening 116 may be absent.

Prosthesis 10 and trial template 100 may be included in a kit. Such kit may also include other prostheses and trial templates of different sizes. Moreover, the kit can include a third component or second shell prosthesis (not shown). Second prosthesis is similar to first shell prosthesis 10 with the difference being that it is configured for implantation in an opposite sided bone. In this regard, second prosthesis is a mirror image of first prosthesis 10. Thus, the kit may include first prosthesis 10, the second prosthesis, and trial template 100 where trial template 100 corresponds to both the first and second prostheses and where the first and second prostheses are configured for opposing variants of a bone. In addition, multiples of this grouping (i.e., first and second prostheses and trial template 100) may be provided with differing sizes to accommodate patients of all sizes. Thus, it should be clear that the more sizes that are provided in the kit, the less clutter trial template 100 minimizes relative to a trial that is not universal. However, it is contemplated that a trial template, similar to template 100, may be provided that is configured only for one variant of bone (i.e., right or left) without departing from the scope of this disclosure. In this regard, the template would not include members 124a-e or 125a-e creating more space for visualization.

In a method of using trial template 100, an operator gains access to a bone cavity that comprises a joint, such as a hip or shoulder joint. The acetabulum, or glenoid, is prepared, such as by using a reamer to resect the bone for reception of prosthesis 10. Once the bone is prepared and ready for trialing, trial template 100 is placed into the bone cavity such that arm members 114*a-c* contact the underlying bone. Such placement may be aided with a guide rod extending from the acetabulum. In this regard, trial template 100 may be placed over the guide rod such that the guide rod extends through cylindrical opening 116. Trial template 100 is rotated into an appropriate orientation relative to the bone using alignment markings 104*a* or 104*b*, depending on the bone it is being inserted into. In this regard, where trial template 100 is placed into a left acetabulum, second alignment marking 104*b* may be oriented so that such marking points in a superior direction or is aligned with a marking previously made in the bone, for example. Alternatively, where trial template 100 is placed into a right acetabulum, first alignment marking 104*a* may be oriented in a similar manner.

Once the trial template 100 is appropriately oriented, operator views the underlying bone via viewing windows 108*a-b* to assess the bone quality beneath template 100 and to assess the fit of trial 100 within the bone. Moreover, when viewing the underlying bone through first window 108*a*, the operator can visualize the locations in which bone screws will be inserted by looking at visualization members 124 or 125 relative to the bone. The center point of their insertion lies along the visualization members 124 or 125. Thus, the operator can assess the bone quality around visualization members 124 or 125 to determine the bone quality at the insertion locations of the bone screws to determine if remedial measures should be taken. Once trial 100 is removed from the bone, prosthesis 10 is inserted into the bone at the same orientation as that of trial template 100 so that tool openings 38*a-e* are positioned at the previously visualized screw insertion regions. Pilot holes may then be drilled into the bone through prosthesis 10 and bone screws inserted therein in order to fix prosthesis 10 to the bone.

As described above, trial template 100 includes visualization members 124, 125 that correspond to tool openings of alternative prostheses. However, visualization members 124, 125 may also correspond to tool openings of one or more drill guides. In other words, in some embodiments, no pilot holes are pre-drilled into bone, or, in other embodiments, a pilot hole is drilled through prosthesis 10 after such prosthesis 10 has been press-fit or otherwise temporarily secured to the underlying bone. In either circumstance, the prosthesis 10 itself at least partially acts as a drill guide. However, in other circumstances, a drill guide with multiple drill openings may be used separately to drill pilot holes at predetermined locations as dictated by the structure of the guide before prosthesis 10 is implanted and secured to the bone. An exemplary drill guide can be found in U.S. Pat. No. 5,769,856, the disclosure of which is incorporated herein by reference in its entirety. In this regard, template 100 may be used similarly to visualize the underlying bone before the drill guide is used to drill pilot holes. Thus, where a drill guide is utilized, visualization members 124 or 125 would correspond to both the tool openings 38 of the prosthesis as well as tool openings of the drill guide.

In addition, while trial template 100 was described as including visualization members 124*a-e* or 125*a-e* that correspond to tool openings 38*a-e*, but not tool openings 39, another embodiment of trial template 100 can include further visualization members (not shown) to correspond to tool openings 39. In this regard, visualization members may extend between an arm member 114*a-c* of distal portion 118 of trial 100 and either first or second support members 122, 126 of proximal portion 119 so as to indicate a line along which bone screws may be inserted into the bone. This would allow an operator to utilize second visualization opening 108*b* to inspect the bone through which bone screws extending through tool openings 39 would be inserted.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An arthroplasty system comprising: a first component having a convex side configured to engage one of an acetabulum and glenoid cavity, a concave side opposite the convex side, a first component periphery defining an outer perimeter of the first component and being defined by a convergence of the convex and concave sides, and a tool opening extending through the first component from the concave side to the convex side and being configured to receive at least one of a bone screw or drill bit, the tool opening having a center point defined by an axis extending along a length of the tool opening; and a second component separate from the first component having a bone facing side, a visualization side opposite the bone facing side, and a second component periphery defining an outer perimeter of the second component that substantially corresponds to the first component periphery, the second component also having first and second support members and a first visualization member, the first and second support members each being arcuate and having a length extending in a direction transverse to an axis that extends through the bone facing and visualization sides within the second component periphery, the first support member partially comprising the second component periphery, and the first and second support members defining a viewing window therebetween that extends through the second component from the visualization side to the bone facing side, the first visualization member being elongate and extending straight along a longitudinal axis that extends from the first support member to the second support members across the viewing window, wherein the first visualization member has a position relative to the second component periphery that corresponds with a position of the center point of the tool opening relative to the first component periphery such that the position of the center point of the tool opening is intersected by the longitudinal axis of the first visualization member when the first component is overlaid with the second component.

2. The arthroplasty system of claim 1, wherein the first component is a drill guide.

3. The arthroplasty system of claim 1, wherein the first component is a prosthesis that includes an articular surface at the concave side.

4. The arthroplasty system of claim 3, wherein the concave side further includes a rim extending at least partially about a concave opening, the tool opening of the first component extending through the rim and the convex surface.

5. The arthroplasty system of claim 1, further comprising a second visualization member adjacent the first visualization member.

6. The arthroplasty system of claim 5, further comprising a third component having a tool opening extending therethrough from a convex side to a concave side thereof, wherein the second visualization member corresponds to the tool opening of the third component where the first component is configured for engagement with a right acetabulum or glenoid cavity and the third component is configured for engagement with a left acetabulum or glenoid cavity.

7. The arthroplasty system of claim 6, wherein the visualization side of the second component includes a right acetabulum or glenoid cavity indicator associated with the first visualization member, and a left acetabulum or glenoid cavity indicator associated with the second visualization member.

8. The arthroplasty system of claim 1, wherein the first visualization member is integrally connected to the first support member and to the second support member.

9. The arthroplasty system of claim 1, wherein the viewing window is crescent shaped.

10. The arthroplasty system of claim 1, wherein the first component is an acetabular cup.

* * * * *